(12) United States Patent
Luongo et al.

(10) Patent No.: US 7,992,425 B2
(45) Date of Patent: Aug. 9, 2011

(54) HYDROGEN SENSOR

(75) Inventors: Kevin Luongo, St. Petersburg, FL (US); Shekhar Bhansali, Tampa, FL (US)

(73) Assignee: University of South Florida, Tampa, FL (US)

( * ) Notice: Subject to any disclaimer, the term of this patent is extended or adjusted under 35 U.S.C. 154(b) by 788 days.

(21) Appl. No.: 11/467,341

(22) Filed: Aug. 25, 2006

(65) Prior Publication Data

US 2007/0108052 A1    May 17, 2007

Related U.S. Application Data

(60) Provisional application No. 60/711,185, filed on Aug. 25, 2005.

(51) Int. Cl.
*G01N 30/00* (2006.01)
*G01N 27/12* (2006.01)
(52) U.S. Cl. ............ 73/31.06; 422/88; 422/98; 977/957
(58) Field of Classification Search .................. 73/23.2, 73/31.05, 31.06; 422/50, 83, 88, 98; 977/902, 977/932, 953, 957
See application file for complete search history.

(56) References Cited

U.S. PATENT DOCUMENTS

| 5,367,283 | A | 11/1994 | Lauf et al. | |
| 5,670,115 | A | 9/1997 | Cheng et al. | |
| 6,450,007 | B1 | 9/2002 | O'Connor | |
| 7,171,841 | B2 * | 2/2007 | Xu et al. | 73/23.2 |
| 2006/0112756 | A1 | 6/2006 | Xu et al. | |

OTHER PUBLICATIONS

C. Tsamis et al., Hydrogen Catalytic Oxidation Reaction on Pd-Doped Porous Silicon, 2 IEEE SENS. J. 89-95 (2002).*
D.R. Baselt et al., Design and Performance of a Microcantilever-Based Hydrogen Sensor, 88 Sensors and Actuators B 120-131 (2003).*
H. Lin et al., A Porous Silicon-Palladium Composite Film for Optical Interferometric Sensing of Hydrogen, 20 Langmuir 5104-5108 (2004).*
F. Rahimi et al., Characterization of Porous Poly-Silicon Impregnated with Pd as a Hydrogen Sensor, 38 J. Phys. D: Appl. Phys. 36-40 (2005).*
F. Favier, E Walter, M. Zach, I. Benter, R. Penner, "Hydrogen sensors an switches from electrodeposited palladium mesowire rays," Science 293 (Sep. 2001) 2227-2231.
M. Lach, K. Ng, R. Penner, "Molybdenum nanowires by electrodeposition," Science 290 (2000) 2120-2123.
V. Polishchuk, E. Souteyrand, J. Martin, V. Strikha, V. Skryshevsky, "A study of hydrogen detection with palladium modified porous silicon," Anal. Chim. Acta 375 (1998) 205-210.
K. Luongo, S. Aravamudhan, S. Bhansali, "A novel approach to integrating nanowires to transductors, without surface contamination," in: Proceedings of the IMAPS Fifth Topical Technology Workshop on MEMS, Related Microsystems and Nanopackaging, Boston, Nov. 20-22, 2003.
Christos Tsamis, Loukis Tsoura, Androula G. Nassiopoulou, Anastasios Travlos, Constantinos E. Salmas, Kostas S. Hatzilyberis, and George P. Androutsopoulos, "Hydrogen Catalytic Oxidation Reaction on Pd-Doped Porous Silicon," IEEE Sensors Journal, vol. 2, No. 2, Apr. 2002, p. 89-94.
Luongo, K., Sine, A., Ortiz, O., and Bhansali, S. Development of a highly sensitive porous Si-based hydrogen sensor using Pd nanostructures. Sensors and Actuators B, 2005.

* cited by examiner

*Primary Examiner* — Randy Boyer
(74) *Attorney, Agent, or Firm* — Michele L. Lawson; Smith & Hopen, P.A.

(57) ABSTRACT

A novel, resistance-based porous silicon sensor with Pd nano structures as the hydrogen sensing layer is presented. The sensor operates at room temperature. The hydrogen sensor of the present includes a p-Type Si substrate that is subjected to porous Si etching to form a nanoporous substrate. The substrate is then coated with a thin layer of Pd and annealed at 900 degrees C. This results in some Pd getting oxidized on porous Si and a thin PdO layer forms on the surface of the substrate. The sensor in accordance with the present invention exhibits an inverse relationship between increased hydrogen concentration versus resistance.

19 Claims, 8 Drawing Sheets

Table 1
EDS spectrum of the sensor surface

| Element | wt.% | at.% | K-ratio |
|---|---|---|---|
| O K | 30.33 | 45.9 | 0.1669 |
| Si K | 60.28 | 51.96 | 0.5775 |
| Pd L | 9.40 | 2.14 | 0.0681 |
| Total | 100.0 | 100.0 | |

The spectrum shows a significant presence of the oxygen.

HYDROGEN SENSOR

CROSS REFERENCE TO RELATED APPLICATIONS

This application claims priority to currently U.S. Provisional Patent Application 60/711,185, entitled, "High Sensitivity Hydrogen Sensor", filed Aug. 25, 2005.

STATEMENT OF GOVERNMENT INTEREST

This invention was made with Government support under Grant No. 0403800 and 0239262 awarded by the National Science Foundation. The Government has certain rights in the invention.

BACKGROUND OF THE INVENTION

The need for a hydrogen sensor with high sensitivity, fast regeneration, and an even faster response time is gaining momentum as efforts to develop a hydrogen economy continue to grow. Numerous companies and organizations such as NASA and DOE, that use large quantities of hydrogen and oversee the development of the technology, have outlined a detailed performance criterion for an acceptable hydrogen sensor. Numerous approaches are being investigated to develop these hydrogen sensors, including sol-gel-based sensors, semiconductor sensors, oxide-based sensors, thin-film-based sensors and acoustic wave sensors. These techniques generally either require a lot of power, show a slow response time or lack the required sensitivity. Recently nanowire-based sensors for detecting hydrogen have been reported. These sensors nanowire-based sensors have been shown to respond in real time. However they lack the sensitivity needed and do not respond to low concentrations of hydrogen. Additionally, the techniques used to fabricate these nanowire sensors require complex procedures, such as the transfer of nanostructures and their organized assembly. These complex fabrication methodologies add to the cost of manufacture making nanowire sensors unsuitable for commercial production.

Porous silicon substrates have been employed in the past to build functional hydrogen sensors. Hydrogen sensors are known in the art wherein the absorption of hydrogen results in the expansion of a palladium (Pd) lattice and a change in the refractive index results such that hydrogen can be detected using optical interferometric techniques.

Palladium is an ideal material for hydrogen sensing because it selectively absorbs hydrogen gas and forms a chemical species known as a palladium hydride. Thick-film hydrogen sensors are known in the art that rely on the fact that palladium metal hydride's electrical resistance is greater than the metal's resistance. In such systems, the absorption of hydrogen is accompanied by a measurable increase in electrical resistance. The resistance increase is caused by the increased resistivity of palladium hydride relative to pure palladium.

By contrast, palladium thin-film sensors as are known in the art are based on an opposing property that depends on the nanoscale structures within the thin film. In the thin film, nanosized palladium particles, or nanoclusters, swell when the hydride is formed, and in the process of expanding, some of the nanoclusters form new electrical connections with neighboring nanoclusters. The increased number of conducting pathways results in an overall net decrease in resistance.

In view of the palladium based sensors known in the art, it is desirable to provide a device that is sensitive to hydrogen, and in particular a hydrogen gas sensor that is easy to fabricate and that exhibits fast regeneration, high sensitivity and a fast response time.

SUMMARY OF INVENTION

The present invention provides for a hydrogen sensor having a fast response time in the presence of hydrogen and also a fast response time to the dissipation of hydrogen.

The present invention addresses the need for a hydrogen sensor with high sensitivity, fast regeneration, and an even faster response time. The method of constructing the hydrogen sensor in accordance with the present invention will lower production costs. The lower cost of production will lower the cost of the finished product to the customer, thereby providing for a cost effective safety measure implementation where hydrogen is produced and/or used.

In a particular embodiment, the present invention provides a new impedance based, Pd/PdO nanoparticle based porous silicon sensor fabricated for low level hydrogen detection.

In accordance with the present invention, Pd nanoparticle structures are fabricated on porous Si by controlled deposition and annealing. In the present sensor, Pd is chosen as the active sensing element as it can adsorb up to 900 times its volume of hydrogen gas. The adsorption of hydrogen causes a swelling of the Pd changing its electrical properties. Unlike the previously reported sensors, this sensor operates at room temperature.

In a particular embodiment, a sensor for hydrogen is provided including a nanoporous silicon substrate, a hydrogen absorbing layer positioned on a surface of the silicon substrate, the hydrogen absorbing layer having a plurality of hydrogen-absorbing nanoclusters positioned within the nanopores of the substrate, at least some of the nanoclusters separated from neighboring nanoclusters by voids and a mechanism in electrical communication with the hydrogen absorbing layer for sensing a change in electrical resistance in response to the presence of hydrogen in contact with the hydrogen absorbing layer, whereby hydrogen absorbed by the hydrogen absorbing layer causes the nanoclusters to expand resulting in a decrease in the voids between the nanoclusters and a corresponding increase in the conductivity of the hydrogen absorbing layer.

In addition to absorption, the sensor in accordance with the present invention also experiences desorption in the absence of hydrogen, whereby the hydrogen-absorbing nanoclusters desorb hydrogen in the absence of hydrogen, thereby causing the nanoclusters to contract resulting in an increase in the voids between the nanoclusters and a corresponding decrease in the conductivity of the hydrogen absorbing layer.

In a specific embodiment, the substrate for the hydrogen sensor is a silicon substrate having a low resistivity and the hydrogen absorbing layer is comprised of palladium and palladium alloys. However, other hydrogen sensing metals are within the scope of the present invention. Including, but not limited to Cu, Au, Ni, Rh, Pt, Y and La or alloys thereof.

A method for sensing hydrogen in accordance with the present invention is also provided in which a nanoporous silicon substrate having a hydrogen absorbing layer positioned on a surface of the silicon substrate is provided. The hydrogen absorbing layer of the substrate includes a plurality of hydrogen-absorbing nanoclusters positioned within the nanopores of the substrate, whereby at least some of the nanoclusters are separated from neighboring nanoclusters by voids. As such, the method includes sensing a change in electrical resistance in response to the presence of hydrogen in contact with the hydrogen absorbing layer, whereby hydrogen absorbed by the hydrogen absorbing layer causes the nanoclusters to expand resulting in a decrease in the voids between the nanoclusters and a corresponding increase in the conductivity of the hydrogen absorbing layer. Additionally, the hydrogen-absorbing nanoclusters desorb hydrogen in the absence of hydrogen, thereby causing the nanoclusters to contract resulting in an increase in the voids between the nanoclusters and a corresponding decrease in the conductivity of the hydrogen absorbing layer.

A method of fabricating a hydrogen sensor in accordance with the present invention is also provided including the steps of forming a nanoporous silicon substrate by electrochemical etching a silicon substrate, depositing a first layer of palladium on a surface of the nanoporous silicon substrate, annealing the first layer of deposited palladium, diffusing the palladium into the nanoporous silicon to form nanoclusters of palladium oxide on the nanoporous silicon substrate and depositing a second layer of palladium on the surface of the nanoporous silicon substrate.

In a specific embodiment, electron beam deposition techniques are used to deposit the palladium layers and the annealing is accomplished in an argon flow at 900° C.

As such, the present invention presents an easy to fabricate, resistance-based porous Si sensor with Pd nanostructures as the sensing layer that responds to low concentrations of hydrogen in real time. The porous Si etching process is a controlled electrochemical etching process that results in islands of Si, nanometers apart. The thin layer of Pd on the surface of these Si islands acts as a sensing layer. The porous Si etching converts the Si surface to a layer with very high electrical impedance. As Pd on top of this high impedance layer absorbs hydrogen, its volume expands bringing it in contact with neighboring Pd, dramatically reducing this impedance. The change in impedance is correlated to hydrogen concentration. The large surface to volume ratio in Pd nanoparticles in this sensor maximizes the hydrogen adsorption area, while minimizing the diffusion of hydrogen due to reduced thickness of the particles. This results in higher sensitivity, faster response and shorter desorption times. As the sensor is built on a silicon substrate, it lends itself to easy integration into sensor arrays or "system on a chip".

BRIEF DESCRIPTION OF THE DRAWINGS

For a fuller understanding of the invention, reference should be made to the following detailed description, taken in connection with the accompanying drawings, in which:

FIG. 8 is a table illustrating the Energy Dispersive Spectroscopy (EDS) for the Pd-based sensor in accordance with the present invention.

DETAILED DESCRIPTION OF THE PREFERRED EMBODIMENT

Figure 1:
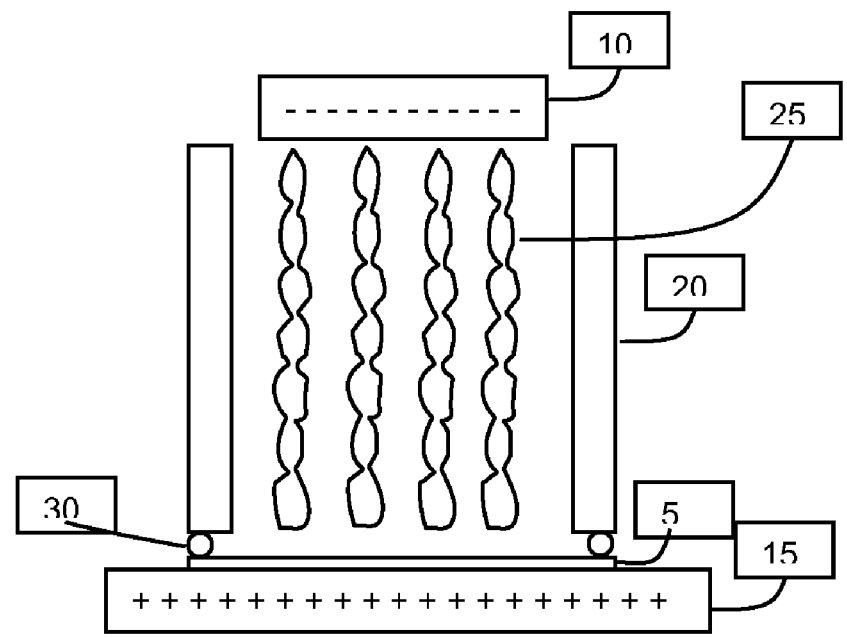
FIG. 1 is a schematic illustration of the porous silicon etching setup in accordance with the present invention.

With reference to FIG. 1, in a particular embodiment, the porous silicon substrate 5 was fabricated from a p-type (1 0 0) silicon wafer of low resistivity (0.001-0.004Ω cm). The wafer 5 was anodized in an electrochemical etching solution 25 consisting of 24% HF/ethanol/$H_2O$. The wafer 5 and platinum cathode 10 were placed in a Teflon jig, having sidewalls 20 and a rubber seal 30, as schematically illustrated in FIG. 1. The surfaces of the Si substrate 5 and Pt cathode 10 were kept parallel to each other and the current flow in the etchant 25 was normal to the wafer surface. The wafer 5 was etched at a current density of 25 $mA/cm^2$ for an hour. The wafer was then removed from the etching bath, rinsed with water, and cleaned. This resulted in formation of an array of nanopores normal to the wafer, all being substantially parallel to each other.

Figure 2:
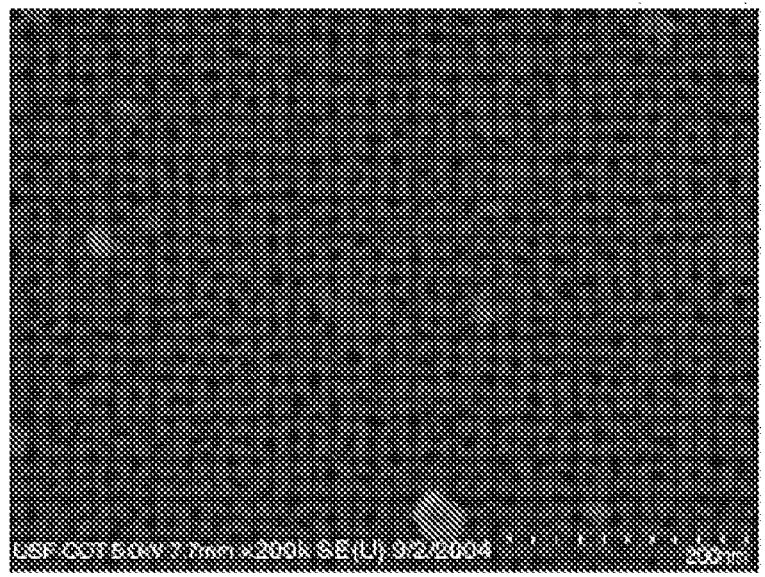
FIG. 2 is an illustration of the (a) surface and (b) cross-section of the substrate immediately after electrochemical etching of the substrate in accordance with the present invention.
Figure 2:
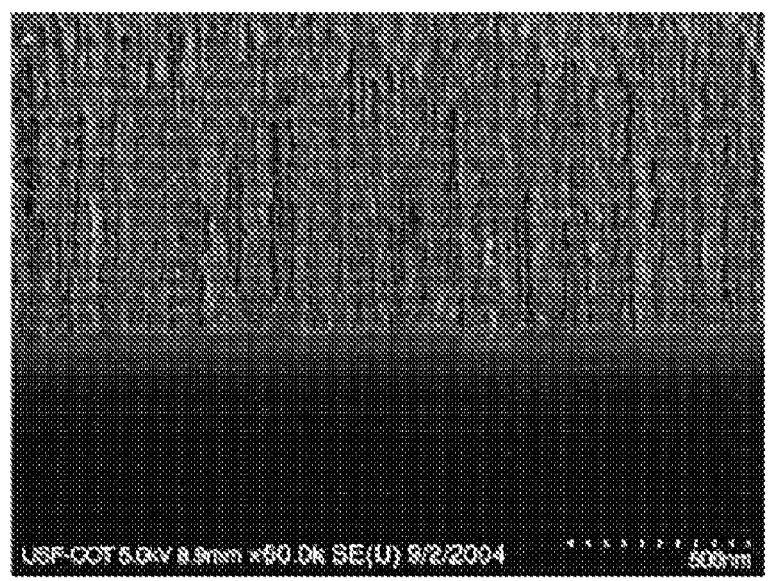

FIG. 2 shows the (a) surface and (b) cross-sectional Scanning Electron Micrograph (SEM) of the wafer following the porous Si etching procedure. FIG. 2a illustrates the distribution of the nanopores. It can be seen that the average pore diameter is about 10 nm. FIG. 2b shows that the pores are oriented normal to the wafer and branching. The branching results in an increase in baseline resistivity. The porous-Si bulk Si-interface is clearly visible in this illustration.

Next, the wafer was placed in an electron-beam evaporator and vacuum stabilized at $10^{-9}$ Pa. Four nanometers of Pd was deposited over the porous Si side of the substrate 5. The Pd thin film was then stabilized on the porous-Si surface through an annealing process. A modified annealing cycle was used to ensure no Pd depletion took place on the substrate 5. The sample was placed in a tube furnace and annealed at 900 degrees C. for 60 minutes. FIG. 3a shows the SEM of the surface after Pd deposition and annealing. FIG. 3b shows the cross-section of the wafer. It can be seen that a Pd rich layer that is not metallic has formed on the surface of porous Si to about 1.4 µm. This Pd rich layer on the surface of the porous-Si acts as an interface between the substrate and Pd nanoparticles on the surface. FIG. 3a shows that the Pd/porous Si structure agglomerates have a diameter of about 50 nm. Next Pd was again evaporated on the porous side, on top of the agglomerates that have been formed, to increase the surface functionality.

The porous silicon sensor in accordance with the present invention was tested for its response to hydrogen using a custom testing chamber was attached to a control system to make the test bed. The chamber was designed to firmly hold the sample to a four-point probe configuration while maintaining the gas composition under investigation. The chamber was connected to the gas inlet line that came from the mass flow controllers. Four MKS model 1479 mass flow controllers (MFCs) of different ranges were used in combination with a MKS type 247 controller to control the hydrogen nitrogen ratio. An exhaust tube located at the opposite side of the chamber was used to feed the expelled gas to a fume hood where it was safely disposed. National Instruments Labview™ program was used to control the mass flow controllers, meter and record the hydrogen-nitrogen concentration.

A Keithley model 2010 multimeter was used to acquire the impedance data. The multimeter was hooked to a computer via a GPIB cable and this data was also acquired using the Labview™ software.

Figure 3:
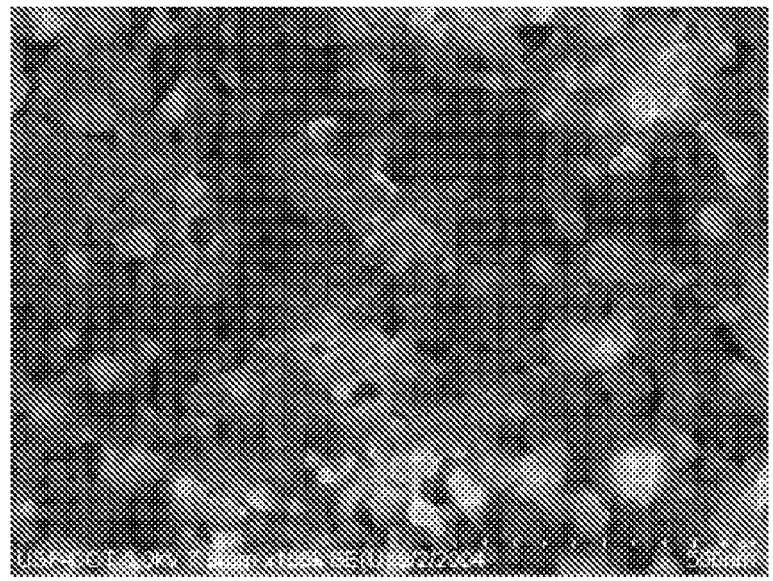
FIG. 3 is an SEM of the surface of the sensor after 4 nm Pd evaporation and diffusion in which (a) illustrates the porosity of the Pd and (b) shows the cross-section after an additional 4 nm Pd is evaporated.
Figure 3:
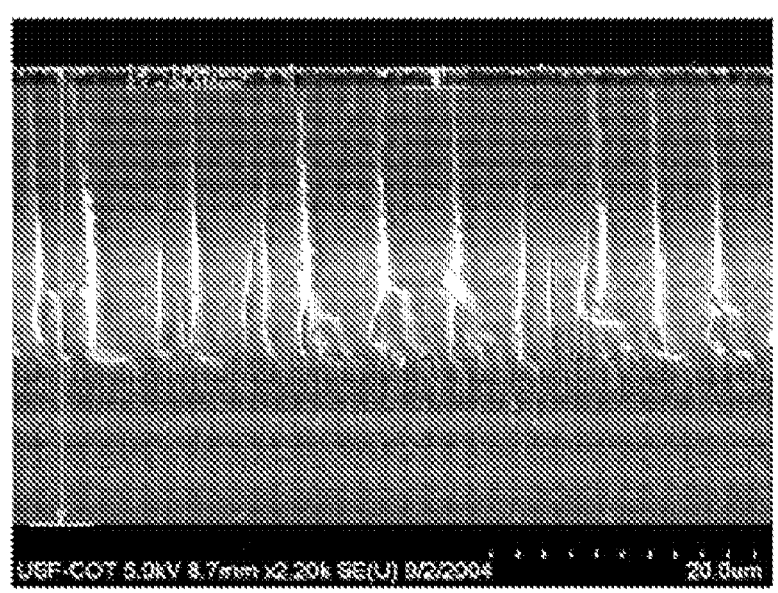
Figure 4:
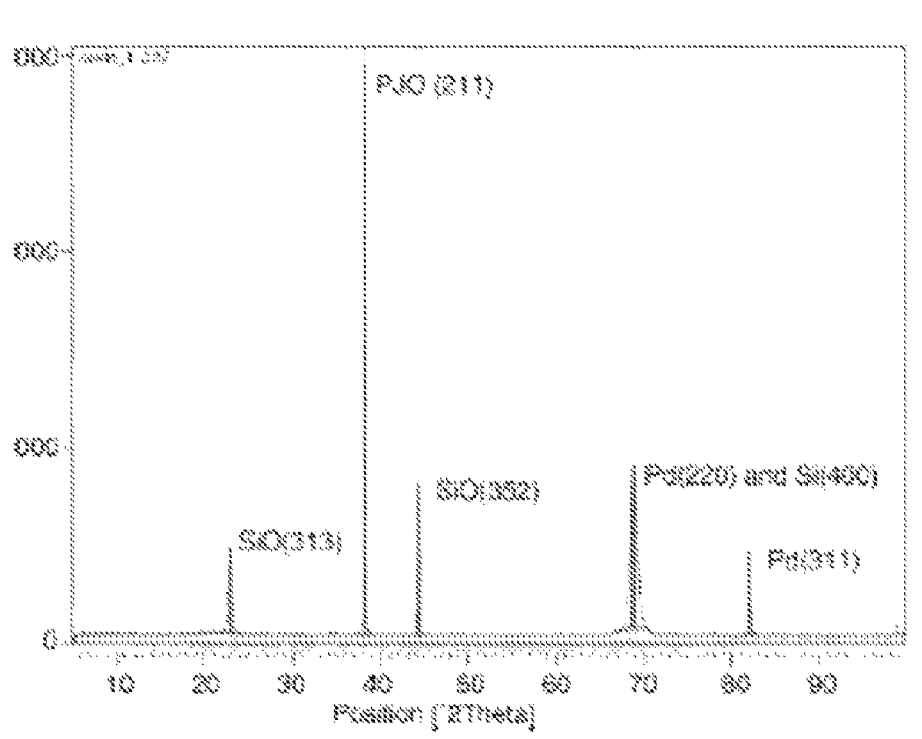
FIG. 4 is a graphical representation of an XRD of Pd-coated porous silicon.

Energy Dispersive Spectroscopy (EDS) spectrum of the sensor was taken to determine the elemental composition of the sensing interface. Table 1 of FIG. 8 shows the EDS data for the film. It can be seen that the sensing surface is rich in oxygen but different from the standard $SiO_2$. X-Ray diffraction (XRD) (FIG. 4) was taken to determine the composition of the sensor (FIG. 3). The XRD confirms the formation of $SiO_2$ and PdO. Additionally, the peaks of substrate Si and surface Pd can also be seen.

The process of compound formation is the following. Upon annealing, the exposed Si on the surface of the pores oxidizes. Additionally the Pd covering the Si oxidizes to PdO. The additional Pd deposited on the surface remains in the native form. While the Pd directly absorbs hydrogen, PdO gets reduced by hydrogen and may return to Pd and contribute to the sensing of the hydrogen. In this film process the reduction of PdO to Pd takes place at 100 degrees C. The present sensor is operated at room temperature and the possibility of room temperature conversion is small.

Figure 5:
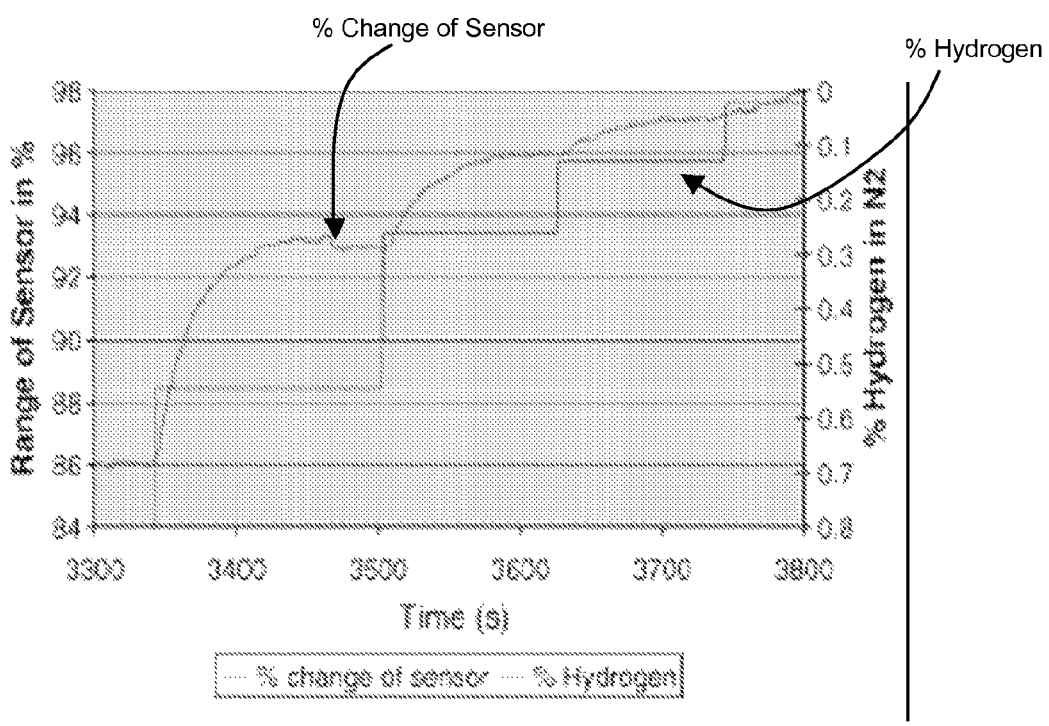
FIG. 5 is a graph illustrating the response of the Pd-based sensor when the percent hydrogen is increased from zero to 0.9% in four steps in accordance with the present invention.
Figure 6:
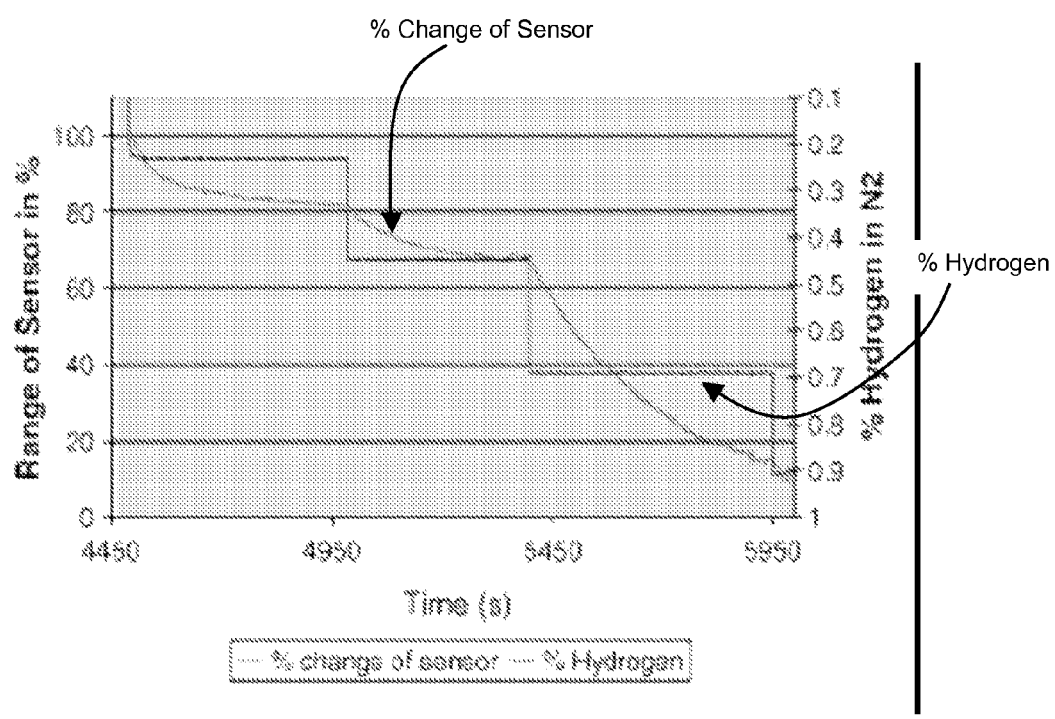
FIG. 6 is a graph illustrating the response of the Pd-based sensor when the percent hydrogen is initiated at 0.8% then decreased in four steps in accordance with the present invention.

The sensor was tested in the setup described and resistivity changes were observed at various percentages of hydrogen in a nitrogen environment between 0 and 1.5% hydrogen. The sensors baseline resistivity was measured to be 2.20 MΩ cm. This large baseline resistivity opposed to that from the starting wafer is consistent with the formation of oxide and the porous nature of the substrate. The percentage change in resistivity as a function of hydrogen concentration in nitrogen is presented in FIGS. 5 and 6. The left side of FIGS. 5 and 6 depict the percentage change in resistivity calculated as:

$$\frac{\rho - \rho\text{MIN}}{\rho\text{MAX} - \rho\text{MIN}} \times 100,$$

where ρ is resistivity, ρMAX the baseline resistivity (percent hydrogen=zero) and ρMIN the resistivity at saturation. The right hand side depicts the percentage of hydrogen in nitrogen. The figures show that the sensor responds to concentration changes of hydrogen in real time both with increasing concentrations and decreasing concentrations.

The sensor response is significantly better than those reported in the prior art. The porous Si template is the key to this stability and sensor performance. The porous Si template serves two purposes; it significantly increases the surface area for adsorption of the gas and simultaneously increases the baseline resistivity of the porous-Si film by removing the Si and creating voids. As stated earlier the nanoparticle deposits of palladium on the surface of the substrate swell from the adsorption of hydrogen. When correctly sized and spaced, the particles contact each other when exposed to hydrogen, thereby significantly reducing the resistance of the substrate. There exists a close correlation between the size of the pores/particles and the response of the sensor. This careful sizing is critical in ensuring that as the particles swell; the pores close, thereby increasing the area of contact and reducing the resistivity of the substrate. The point-to-point resistance anywhere on the sensor therefore decreases until the Pd reaches its maximum adsorption or the particle-to-particle contact area reaches a maximum.

Figure 7:
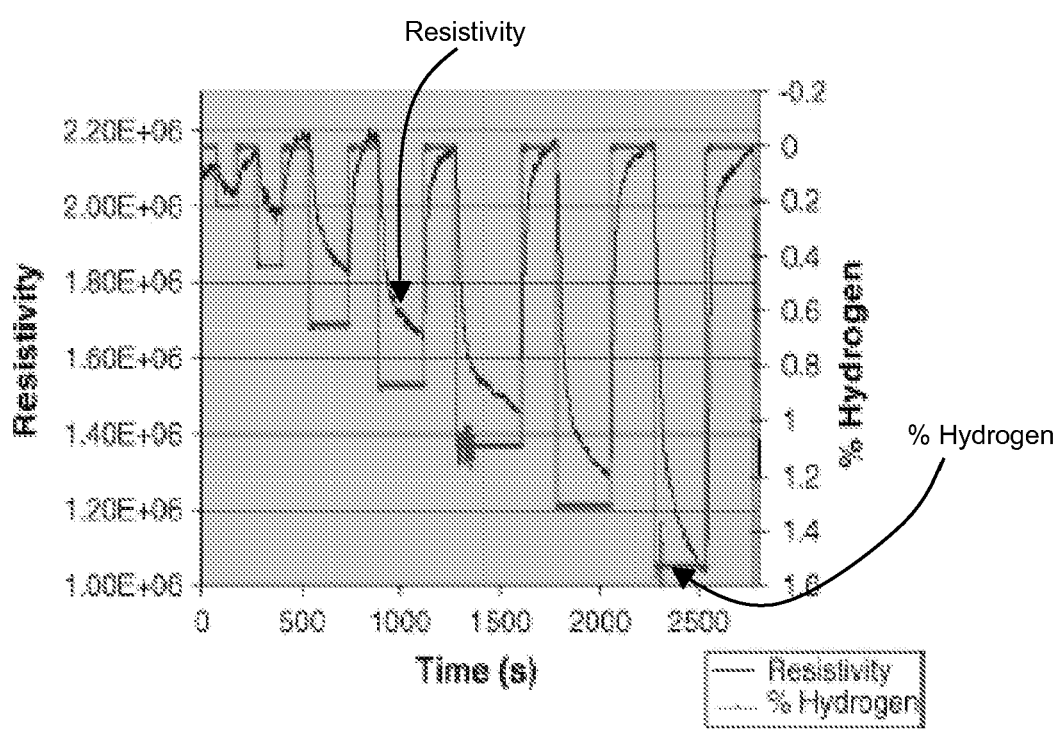
FIG. 7 is a graph illustrating the response of the Pd-based sensor when the percent hydrogen is initiated at zero and increasingly pulsed to different concentrations between 0 and 1.5% and then back to zero.

In an exemplary embodiment to study the sensor response and adsorption and desorption rates, the hydrogen was pulsed back and forth between zero and a random value in the presence of the sensor. The change in resistivity and the concentration of the sensor of the feed gas are shown in FIG. 7. It can be seen in these tests that the adsorption and desorption times of the sensor are less than 2 seconds. Additionally, it can be seen that the sensor maintains a very stable baseline after repeated cycling. This stability and lack of drift is an important feature that is critical for industrial applications.

The slowed rate of change at the bottom and top of the resistivity curves given in FIG. 7 suggests a transfer of hydrogen from easily accessed surface particles to less accessible pore particles, or visa versa, depending on whether the sensor is in adsorption or desorption mode. This observation suggests that the depth of the pores may also influence the response time of the sensor. As such, the diffusion path length is relatively very small and hence the concentration gradient is sufficient.

In accordance with the present invention, a Pd/porous Si sensor for hydrogen detection has been made and tested in the 0-1.5% range. It has been observed that sensors made with porous silicon and palladium nanoparticles demonstrate a significant decrease in resistivity with respect to time when exposed to hydrogen. The Pd nanoparticles decrease the adsorption and desorption times, which increases the sensitivity, sensing, and regeneration times of the sensor. The controlled sizing results in an average response time of less than 2 seconds, for low concentrations of hydrogen. The high selectivity, cost effectiveness and ease of fabrication, Pd/porous silicon has the potential of becoming a truly universal hydrogen sensing system.

It will be seen that the advantages set forth above, and those made apparent from the foregoing description, are efficiently attained and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention which, as a matter of language, might be said to fall therebetween. Now that the invention has been described,

What is claimed is:

1. An electrical resistance-based sensor for low levels of hydrogen comprising:
   a nanoporous silicon substrate having nanopores about 10 nm in diameter wherein the nanopores are positioned normal with respect to the surface of the substrate and exhibit branching;
   a hydrogen absorbing layer positioned on a surface of the silicon substrate, the hydrogen absorbing layer having a plurality of hydrogen-absorbing nanoclusters positioned within the nanopores of the substrate, at least some of the nanoclusters separated from neighboring nanoclusters by voids;
   a metallic layer positioned on the nanoclusters; and
   a mechanism in electrical communication with the hydrogen absorbing layer for sensing a change in electrical resistance in response to the presence of hydrogen in contact with the hydrogen absorbing layer, whereby hydrogen absorbed by the hydrogen absorbing layer causes the nanoclusters to expand resulting in an increase in particle to particle contact between the nanoclusters and a corresponding increase in the conductivity of the hydrogen absorbing layer.

2. The sensor of claim 1, whereby the hydrogen-absorbing nanoclusters desorb hydrogen in the absence of hydrogen in contact with the hydrogen absorbing layer, thereby causing the nanoclusters to contract resulting in a decrease in particle to particle contact between the nanoclusters and a corresponding decrease in the conductivity of the hydrogen absorbing layer.

3. The sensor of claim 1, wherein the substrate is a silicon substrate having a low resistivity.

4. The hydrogen sensor of claim 1, wherein the hydrogen absorbing layer is palladium.

5. The hydrogen sensor of claim 1, wherein the hydrogen absorbing layer is a palladium alloy.

6. The hydrogen sensor of claim 1, wherein the hydrogen-absorbing nanoclusters are palladium oxide nanoclusters.

7. The hydrogen sensor of claim 1, wherein the hydrogen-absorbing nanoclusters have an average diameter of less than about 50 nanometers.

8. The hydrogen sensor of claim 1, wherein the nanopores are substantially parallel to each other.

9. An electrical resistance-based method for sensing low levels of hydrogen, the method comprising the steps of:
    providing a nanoporous silicon substrate having nanopores with a diameter of about 10 nm wherein the nanopores are positioned normal to the surface of the substrate and exhibit branching;
    positioning a hydrogen absorbing layer on a surface of the silicon substrate, the hydrogen absorbing layer having a plurality of hydrogen-absorbing nanoclusters positioned within the nanopores of the substrate, at least some of the nanoclusters separated from neighboring nanoclusters by voids;
    evaporating an additional metallic layer on the nanoclusters; and
    sensing a change in electrical resistance in response to the presence of hydrogen in contact with the hydrogen absorbing layer, whereby hydrogen absorbed by the hydrogen absorbing layer causes the nanoclusters to expand resulting in an increase in particle to particle contact between the nanoclusters and a corresponding increase in the conductivity of the hydrogen absorbing layer.

10. The method of claim 9, further comprising the step of sensing a change in the electrical resistance in response to the absence of hydrogen in contact with the hydrogen absorbing layer, whereby the hydrogen-absorbing nanoclusters desorb hydrogen in the absence of hydrogen, thereby causing the nanoclusters to contract resulting in a decrease in particle to particle contact between the nanoclusters and a corresponding decrease in the conductivity of the hydrogen absorbing layer.

11. A method of fabricating an electrical resistance-based hydrogen sensor for measuring low levels of hydrogen, the method comprising the steps of:
    forming a nanoporous silicon substrate by electrochemical etching a silicon substrate to form nanopores having a diameter of about 10 nm wherein the nanopores are positioned normally in relation to the surface of the substrate and exhibit branching;
    depositing a first layer of palladium on a surface of the nanoporous silicon substrate;
    annealing the first layer of deposited palladium;
    diffusing the first layer of palladium into the nanoporous silicon to form nanoclusters of palladium oxide on the nanoporous silicon substrate; and
    depositing a second layer of palladium on the surface of the nanoporous silicon substrate;
    placing a mechanism in electrical communication with the hydrogen absorbing layer for sensing a change in electrical resistance in response to the presence of hydrogen in contact with the first layer of palladium, whereby hydrogen absorbed by the first layer of palladium causes the nanoclusters to expand resulting in an increase in particle to particle contact between the nanoclusters and a corresponding increase in the conductivity of the first layer of palladium.

12. The method of claim 11, wherein the silicon substrate is a low resistivity p-type silicon substrate.

13. The method of claim 11, wherein the nanopores are positioned parallel to each other.

14. The method of claim 11, whereby the first layer of palladium is deposited using electron beam deposition.

15. The method of claim 11, whereby the first layer of deposited palladium is 4 nm in thickness.

16. The method of claim 11, whereby the first layer of palladium is diffused into the nanoporous silicon substrate in an argon flow at 900 degrees centigrade.

17. The method of claim 11, wherein the step of annealing causes the silicon comprising the nanopores to oxidize.

18. The method of claim 11, wherein the step of annealing causes nanoclusters of palladium oxide to form on the surface of the nanopores of the nanoporous silicon substrate.

19. The method of claim 11, whereby the second layer of palladium is deposited using electron beam deposition.

* * * * *